United States Patent

Ikesu et al.

Patent Number: 5,306,610
Date of Patent: Apr. 26, 1994

[54] PHOTOGRAPHIC COUPLER

[75] Inventors: Satoru Ikesu; Hiroshi Kita; Yutaka Kaneko, all of Hino, Japan

[73] Assignee: Konica Corporation, Tokyo, Japan

[21] Appl. No.: 41,515

[22] Filed: Apr. 1, 1993

Related U.S. Application Data

[63] Continuation of Ser. No. 853,639, Mar. 18, 1992, abandoned.

[30] Foreign Application Priority Data

Apr. 4, 1991 [JP] Japan .................... 3-97861

[51] Int. Cl.⁵ .............................. G03C 7/38
[52] U.S. Cl. ........................ 430/558; 430/384; 430/385
[58] Field of Search ............... 430/558, 384, 385

[56] References Cited

U.S. PATENT DOCUMENTS 4,992,442 12/1991 Tsujitani et al. ............... 544/251

FOREIGN PATENT DOCUMENTS 1-271751 10/1989 Japan ..................... 430/558
2-277050 11/1990 Japan ..................... 430/558

OTHER PUBLICATIONS

Shindo et al, *Heterocycles* 29 p. 899 (1989).

*Primary Examiner*—Lee C. Wright
*Attorney, Agent, or Firm*—Jordan B. Bierman

[57] ABSTRACT

Disclosed is a photographic coupler represented by the formula 1:

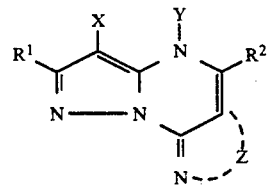

wherein $R^1$, $R^2$ and Y each represent hydrogen atom or a substituent; Z represents a non-metallic atomic group necessary for forming a 5- to 7-membered heterocyclic ring, and said 5- to 7-membered ring may have a substituent(s); and X represents hydrogen atom or a substituent which is eliminatable by the reaction with an oxidized product of a color developing agent, which is used for a light-sensitive silver halide color photographic material and a heat-processable light-sensitive material.

9 Claims, No Drawings

PHOTOGRAPHIC COUPLER

This application is a continuation of Ser. No. 07/853,639, filed Mar. 18, 1992 now abandoned, which claims the priority of Japanese Application 97861/1991, filed Apr. 4, 1991.

BACKGROUND OF THE INVENTION

This invention relates to a novel photographic coupler which is used as a color photographic material, more specifically to a photographic coupler which forms a dye image excellent in fastness to heat, humidity and light.

By subjecting a light-sensitive silver halide photographic material to exposure and then color development processing, an oxidized aromatic primary amine color developing agent and a dye-forming coupler are reacted in an exposed area to form a dye, whereby a color image is formed.

In such a photographic method, a color reproduction method according to a subtractive color system is generally used, and yellow, magenta and cyan color images are formed.

As a photographic coupler used for forming the above yellow color image, there may be mentioned, for example, an acylacetanilide type coupler. As a coupler for forming the magenta color image, there has been known, for example, a pyrazolone, pyrazolobenzimidazole, pyrazolotriazole or indazolone type coupler. Further, as a coupler for forming the cyan color image, there may be generally used, for example, a phenol or naphthol type coupler.

The dye image thus obtained has been demanded to be neither discolored nor faded even if it is exposed to light for a long time or stored at high temperature and high humidity.

However, a phenol type coupler and a naphthol type coupler which have been studied as a coupler for forming a cyan dye are not so satisfactory in the points of spectral absorption characteristics, heat resistance, humidity resistance and light resistance of a cyan dye image formed. For improving these properties, various proposals including change of substituents have been made. For example, a 2,5-diacylphenol type cyan coupler has been disclosed in Japanese Provisional Patent Publication No. 31953/1984; a two-equivalent type naphthol cyan coupler has been disclosed in Japanese Provisional Patent Publications No. 117422/1975 and No. 32071/1980; a cyan coupler having an ureido group at the 2-position of phenol has been disclosed in Japanese Provisional Patent Publication No. 65135/1981; and a cyan coupler having an acyl group at the 5-position of naphthol has been disclosed in Japanese Provisional Patent Publication No. 53643/1986. However, a compound which is satisfactory in all these properties has not yet been obtained.

SUMMARY OF THE INVENTION

Thus, the present inventors have further studied about the above points, and consequently found a photographic coupler which can form a cyan dye image free from color shift caused by heat, humidity and light, to accomplish the present invention.

A first object of the present invention is to provide a novel photographic coupler used as a color photographic material.

A second object of the present invention is to provide a photographic coupler which forms a cyan dye image free from color shift caused by heat, humidity and light.

The above objects of the present invention can be accomplished by a photographic coupler represented by the formula 1:

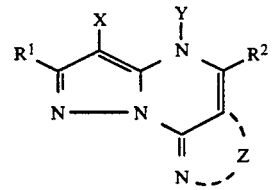

wherein $R^1$, $R^2$ and Y each represent hydrogen atom or a substituent; Z represents a non-metallic atomic group necessary for forming a 5- to 7-membered heterocyclic ring, and said 5- to 7-membered ring may have a substituent(s); and X represents hydrogen atom or a substituent which is eliminatable by the reaction with an oxidized product of a color developing agent.

DESCRIPTION OF THE PREFERRED EMBODIMENTS

In the following, the present invention is explained in detail.

$R^1$ in the formula 1 represents hydrogen atom or a substituent. The substituent represented by $R^1$ is not particularly limited, but may representatively include each group of alkyl, aryl, anilino, acylamino, sulfonamido, alkylthio, arylthio, alkenyl and cycloalkyl. There may be additionally included a halogen atom; each group of cycloalkenyl, alkynyl, heterocyclic ring, sulfonyl, sulfinyl, phosphonyl, acyl, carbamoyl, sulfamoyl, cyano, alkoxy, sulfonyloxy, aryloxy, heterocyclicoxy, siloxy, acyloxy, carbamoyloxy, amino, alkylamino, imido, ureido, sulfamoylamino, alkoxycarbonylamino, aryloxycarbonylamino, alkoxycarbonyl, aryloxycarbonyl, heterocyclicthio, thioureido, carboxy, hydroxy, mercapto, nitro and sulfonic acid; a spiro compound residue; and a bridged hydrocarbon compound residue.

Among the substituents represented by $R^1$, the alkyl group preferably has 1 to 32 carbon atoms, which may be straight or branched.

The aryl group is preferably phenyl group.

The acylamino group includes alkylcarbonylamino group and arylcarbonylamino group.

The sulfonamido group includes alkylsulfonylamino group and arylsulfonylamino group.

As the alkyl component and aryl component in the alkylthio group and arylthio group, there may be mentioned the above alkyl group and aryl group represented by $R^1$.

The alkenyl group preferably has 2 to 32 carbon atoms, and the cycloalkyl group preferably has 3 to 12, particularly 5 to 7 carbon atoms. The alkenyl group may be straight or branched.

The cycloalkenyl group preferably has 3 to 12, particularly 5 to 7 carbon atoms.

The sulfonyl group includes alkylsulfonyl group and arylsulfonyl group.

The sulfinyl group includes alkylsulfinyl group and arylsulfinyl group.

The phosphonyl group includes alkylphosphonyl group, alkoxyphosphonyl group, aryloxyphosphonyl group and arylphosphonyl group.

The acyl group includes alkylcarbonyl group and arylcarbonyl group.

The carbamoyl group includes alkylcarbamoyl group and arylcarbamoyl group.

The sulfamoyl group includes alkylsulfamoyl group and arylsulfamoyl group.

The acyloxy group includes alkylcarbonyloxy group and arylcarbonyloxy group.

The carbamoyloxy group includes alkylcarbamoyloxy group and arylcarbamoyloxy group.

The ureido group includes alkylureido group and arylureido group.

The sulfamoylamino group includes alkylsulfamoylamino group and arylsulfamoylamino group.

The heterocyclic group is preferably 5- to 7-membered, and specifically includes 2-furyl group, 2-thienyl group, 2-pyrimidinyl group, 2-benzothiazolyl group, 1-pyrrolyl group and 1-tetrazolyl group.

The heterocyclicoxy group preferably has a 5- to 7-membered heterocyclic ring, and includes, for example, 3,4,5,6-tetrahydropyranyl-2-oxy group and 1-phenyltetrazol-5-oxy group.

The heterocyclicthio group is preferably a 5- to 7-membered heterocyclicthio group, and includes, for example, 2-pyridylthio group, 2-benzothiazolylthio group and 2,4-diphenoxy-1,3,5-triazol-6-thio group.

The siloxy group includes trimethylsiloxy group, triethylsiloxy group and dimethylbutylsiloxy group.

The imido group includes succinimido group, 3-heptadecylsuccinimido group, phthalimido group and glutarimido group.

The spiro compound residue includes spiro[3,3]heptan-1-yl.

The bridged hydrocarbon compound residue includes bicyclo[2,2,1]heptan-1-yl, tricyclo[3,3,1,1$^{3,7}$]decan-1-yl and 7,7-dimethyl-bicyclo[2,2,1]heptan-1-yl.

$R^2$ represents hydrogen atom or a substituent. The substituent represented by $R^2$ is not particularly limited so long as it is a group which can substitute nitrogen atom, but may representatively include each group of alkyl, aryl, alkenyl, cycloalkyl, cycloalkenyl, alkynyl, heterocyclic ring, sulfonyl, phosphonyl, acyl, carbamoyl and sulfamoyl. As specific examples of these substituents, there may be mentioned the same groups described about $R^1$.

Among the above substituents, $R^2$ is preferably, for example, each group of alkyl, aryl, alkenyl, cycloalkenyl, alkynyl and heterocyclic ring.

The above groups represented by $R^1$ and $R^2$ may further have a substituent(s) such as a ballast group including a long chain hydrocarbon group and a polymer residue.

As the group which is eliminatable by the reaction with an oxidized product of a color developing agent, represented by X, there may be mentioned, for example, a halogen atom (chlorine atom, bromine atom and fluorine atom); and each group of alkoxy, aryloxy, heterocyclicoxy, acyloxy, sulfonyloxy, alkoxycarbonyloxy, aryloxycarbonyl, alkyloxalyloxy, alkoxyoxalyloxy, alkylthio, arylthio, heterocyclicthio, alkyloxythiocarbonylthio, acylamino, sulfonamido, nitrogen-containing heterocyclic ring bonded by N atom, alkyloxycarbonylamino, aryloxycarbonylamino, carboxyl and

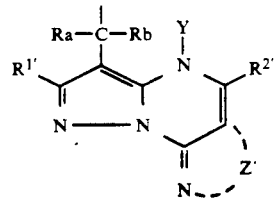

(wherein $R^{1'}$, $R^{2'}$, $Y'$ and $Z'$ each have the same meanings defined as the above $R^1$, $R^2$, Y and Z; Ra and Rb each represent hydrogen atom, an aryl group, an alkyl group or a heterocyclic group), preferably a halogen atom. Among them, the particularly preferred group represented by X is hydrogen atom and chlorine atom.

In the formula 1, Y represents hydrogen atom or a substituent. The substituent represented by Y is preferably, for example, a substituent which is eliminatable from the compound of the present invention after the above compound is reacted with an oxidized product of a developing agent. The substituent represented by Y includes, for example, a group which is eliminatable under alkaline conditions as disclosed in Japanese Provisional Patent Publication No. 228444/1986 and a substituent which undergoes coupling-off by the reaction with an oxidized product of a developing agent as disclosed in Japanese Provisional Patent Publication No. 133734/1981, but Y is preferably hydrogen atom.

Thus, the compound of the present invention represented by the formula 1 is more preferably represented by the formula 3:

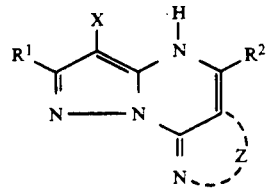

In the formula, $R^1$, $R^2$ and X each have the same meanings as those of $R^1$, $R^2$ and X of the compound represented by the formula 1.

Z represents a non-metallic atomic group necessary for forming a 5- to 7-membered heterocyclic ring. Said 5- to 7-membered heterocyclic ring may have a substituent(s), if necessary.

Said 5- to 7-membered heterocyclic ring may be saturated or unsaturated, and a hetero atom included in said 5- to 7-membered heterocyclic ring is preferably nitrogen atom, sulfur atom and oxygen atom. The compound represented by the above formula 3 may be represented by, for example, the following formula 4 to formula 12, but the compound is not limited to these.

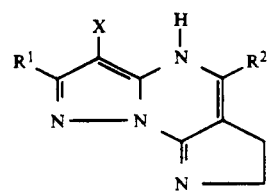

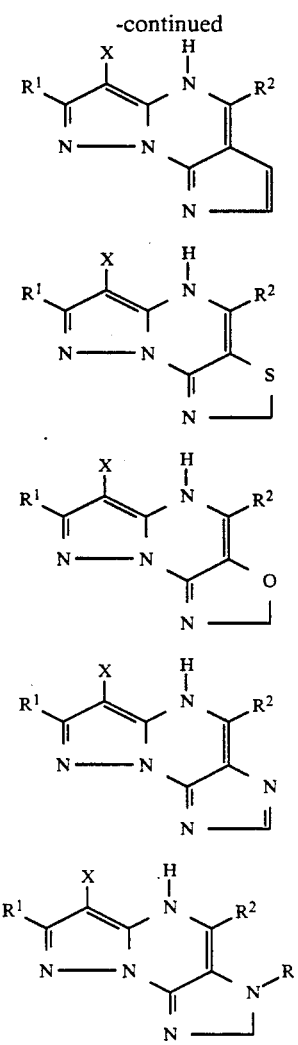
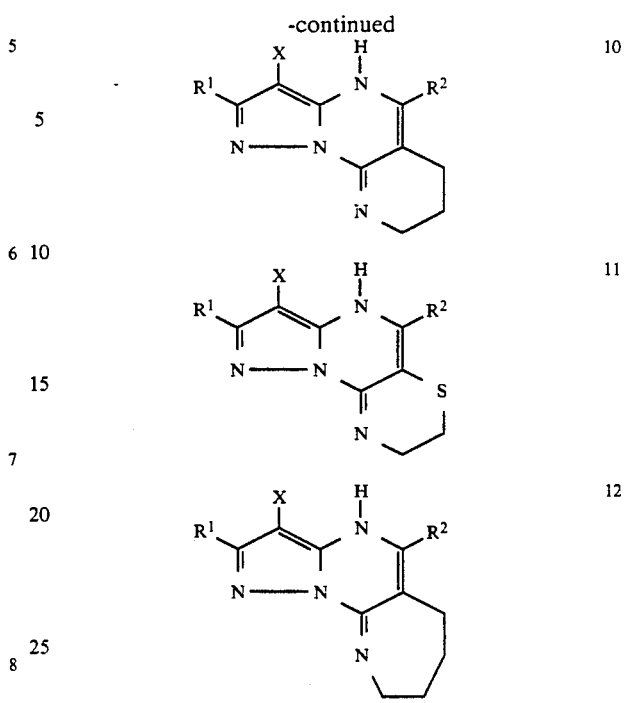

(wherein $R^1$, $R^2$ and X each have the same meanings as those of $R^1$, $R^2$ and X in the formulae 1 and 3; and R represents a substituent specifically including an alkyl group, an aryl group, an alkenyl group, a cycloalkyl group, a sulfonyl group, an acyl group, a carbamoyl group, a sulfamoyl group, an alkoxycarbonyl group and an aryloxycarbonyl group.)

The 5- to 7-membered heterocyclic ring in the formula 4 to the formula 12 may have a substituent(s), if necessary.

The representative compound examples of the present invention are shown below, but the present invention is not limited to these.

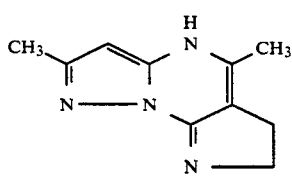

(1)

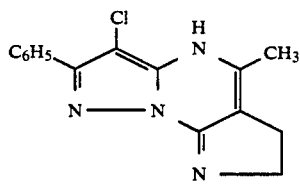

(2)

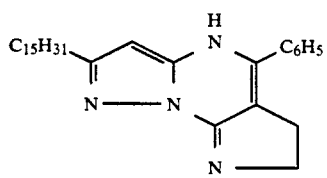

(3)

-continued
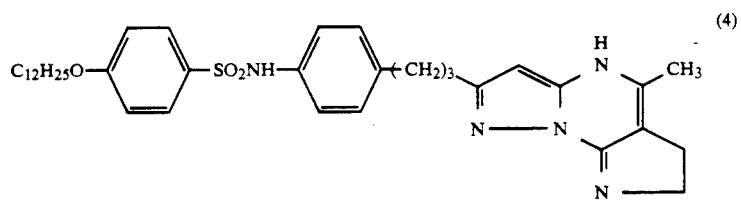
(4)
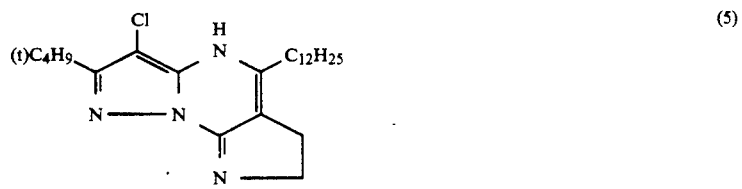
(5)
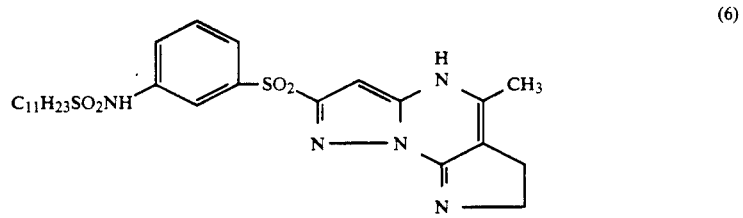
(6)
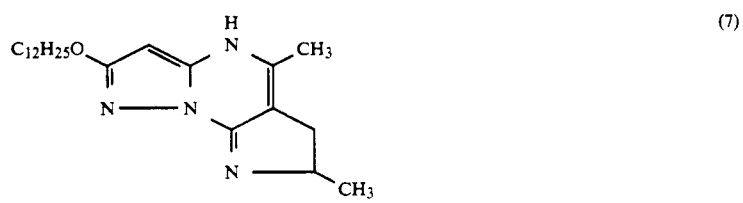
(7)
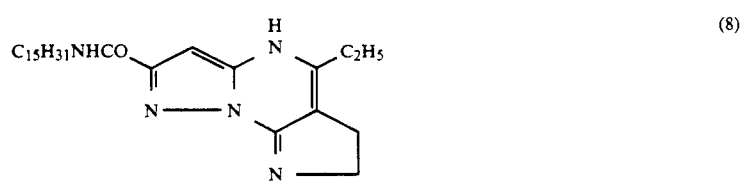
(8)
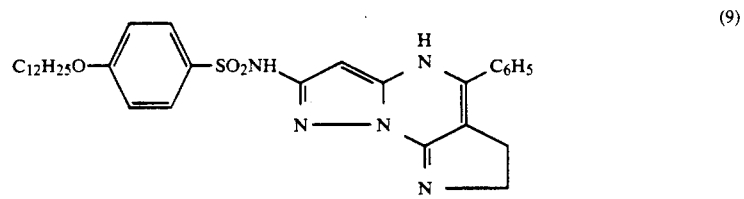
(9)
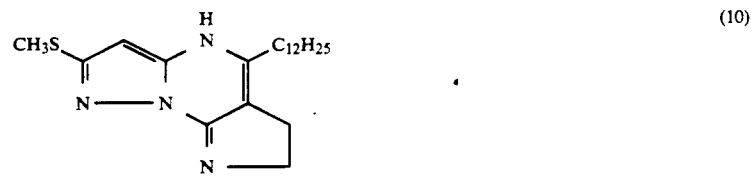
(10)
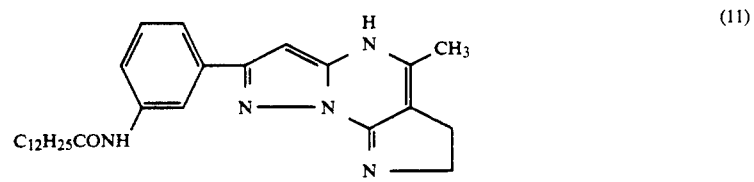
(11)

-continued
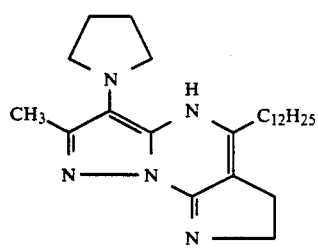 (12)
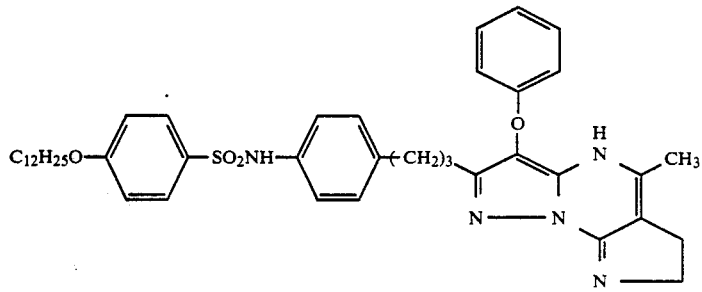 (13)
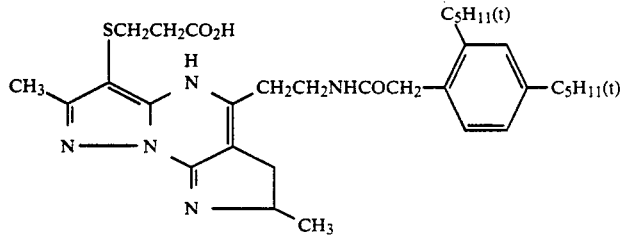 (14)
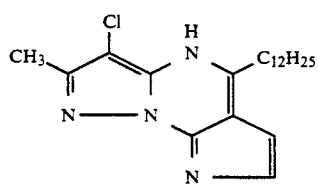 (15)
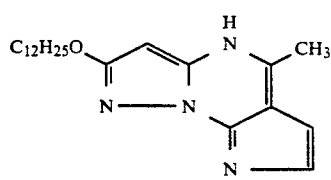 (16)
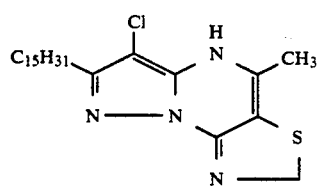 (17)
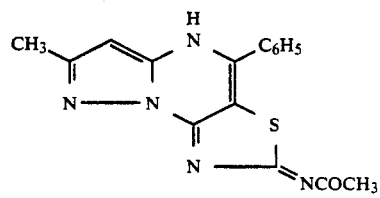 (18)

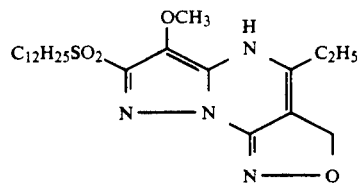 (19)
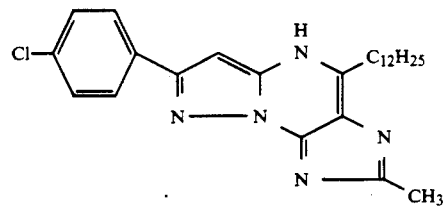 (20)
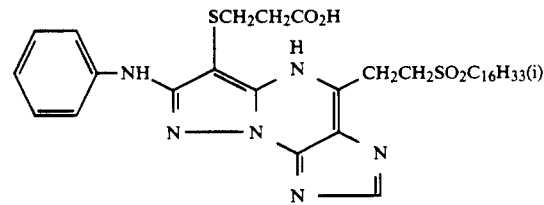 (21)
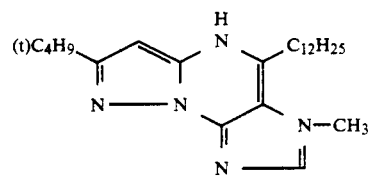 (22)
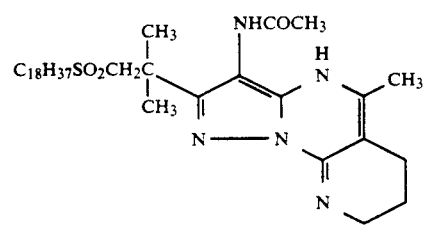 (23)
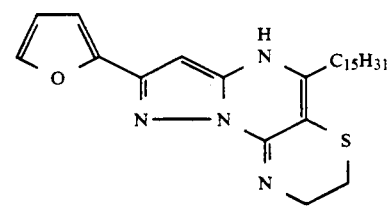 (24)
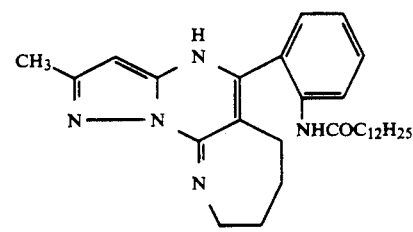 (25)
The above coupler of the present invention can be synthesized easily according to the synthetic methods disclosed in Japanese Provisional Patent Publication No. 275882/1990 and "Sulfur Letter", 1989, Vol. 9 (1-2), page 9 to 16.
In the above cited literatures, there was not disclosed at all that the compounds described in said literature were useful as a color photographic coupler.

Synthetic Example

Synthesis of Exemplary Compound 1

Exemplary compound 1 was synthesized according to the following scheme:

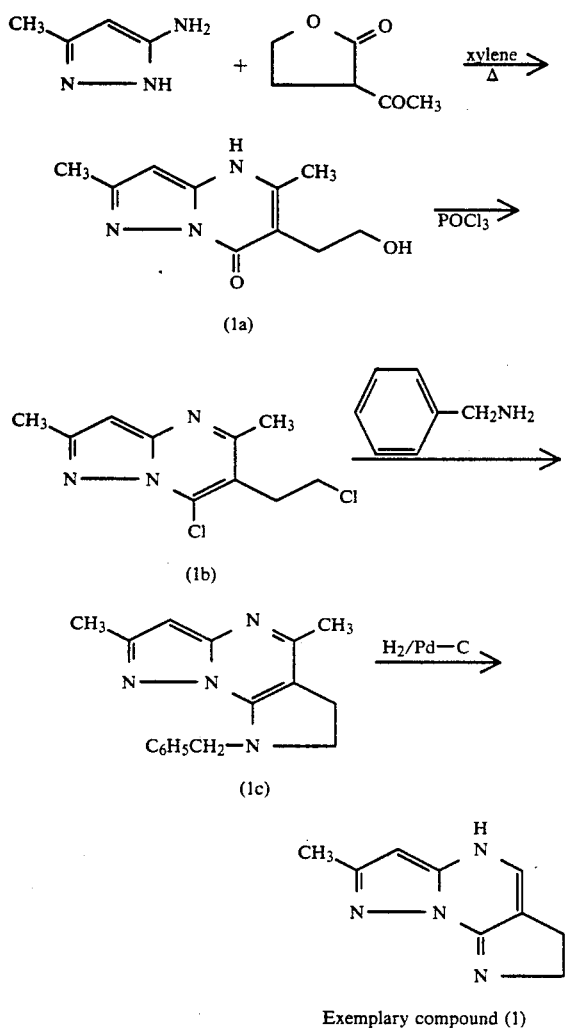

Exemplary compound (1)

(1) Synthesis of Intermediate (1a)

To 50 ml of xylene were added 9.7 g (0.1 mole) of 3-amino-5-methylpyrazole and 12.8 g (0.1 mole) of α-acetyl-γ-butyrolactone, and the mixture was refluxed by heating for 5 hours. After completion of the reaction, the reaction mixture was cooled, and the crystals precipitated were collected by filtration to obtain 10.8 g (yield: 52%) of Compound (1a) which was an intermediate.

(2) Synthesis of Intermediate (1b)

In 60 ml of phosphorus oxychloride was dispersed 20.7 g (0.1 mole) of Compound (1a), and the dispersion was refluxed by heating for 4 hours. After completion of the reaction, phosphorus oxychloride was removed under reduced pressure, and the residue was poured into ice water, neutralized with sodium hydrogen carbonate and then extracted with ethyl acetate.

Subsequently, the solvent was removed under reduced pressure, and the residue was purified by using silica gel column chromatography to obtain 15.4 g (yield: 63%) of Compound (1b) which was an intermediate.

(3) Synthesis of Intermediate (1c)

In 100 ml of ethyl acetate were dissolved 24.4 g (0.1 mole) of Compound (1b), 10.7 g (0.1 mole) of benzylamine and 15.8 g (0.2 mole) of pyridine, and the mixture was refluxed by heating for 4 hours. After completion of the reaction, water was added to the reaction mixture to decompose an organic layer, and the solvent was removed under reduced pressure. Subsequently, the residue was purified by using silica gel column chromatography to obtain 18.9 g (yield: 68%) of Compound (1c) which was an intermediate.

(4) Synthesis of Exemplary compound (1)

In 200 ml of methanol was dissolved 27.8 g (0.1 mole) of Compound (1c), and 3 g of 5% palladium-attached activated carbon was added thereto. The mixture was hydrogenated under 1 atm at room temperature for 5 hours. After completion of the reaction, the catalyst was removed by filtration, and the solvent was removed under reduced pressure. The residue was recrystallized from ethyl acetate to obtain 14.1 g (yield: 75%) of the desired Exemplary compound (1).

The structure was confirmed by $^1$H-NMR and mass spectra.

(2) Synthesis of Exemplary compound (18)

Exemplary compound (18) was synthesized according to the following scheme.

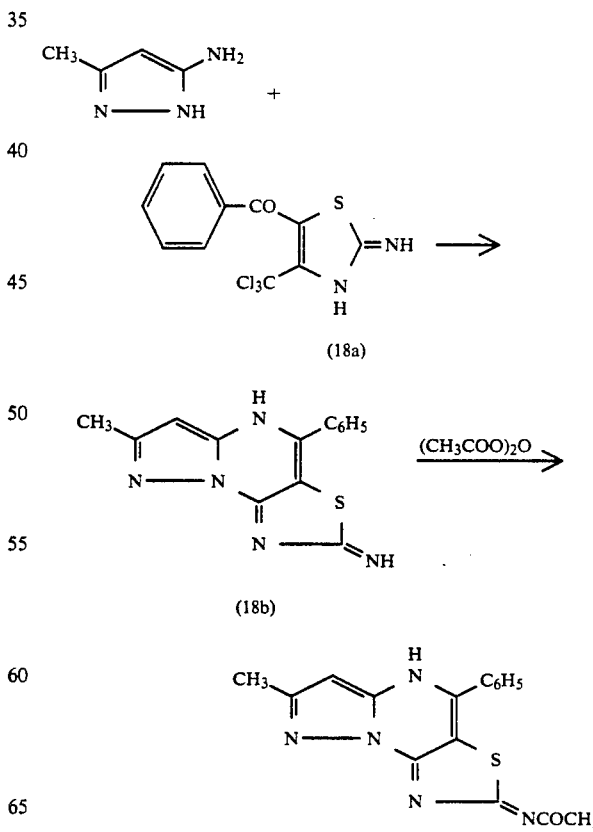

Exemplary compound (18)

(1) Synthesis of Intermediate (18b)

In 100 ml of dioxane were dispersed 9.7 g (0.1 mole) of 3-amino-5-methylpyrazole and 32.1 g (0.1 mole) of Compound (18a), and the dispersion was refluxed by heating for 5 hours. After completion of the reaction, the reaction mixture was cooled, and the crystals precipitated were collected by filtration to obtain 20.0 g (yield: 71%) of Compound (18b) which was an intermediate.

(2) Synthesis of Exemplary compound (18)

In 90 ml of pyridine was dissolved 28.1 g (0.1 mole) of Compound (18b), and 11.2 g (0.11 mole) of acetic anhydride was added dropwise thereto at room temperature. Subsequently, the mixture was reacted at about 80° C. for 2 hours. After completion of the reaction, the reaction mixture was poured into 200 ml of water, and the crystals obtained were collected by filtration. Then, the crystals obtained were further recrystallized from ethanol to obtain 17.4 g (yield: 54%) of the desired Exemplary compound (18).

The structure was confirmed by $^1$H-NMR and mass spectra.

The coupler of the present invention may be generally used in an amount of $1 \times 10^{-3}$ mole to 1 mole, preferably in the range of $1 \times 10^{-2}$ mole to $8 \times 10^{-1}$ mole per mole of silver halide.

Further, the coupler of the present invention may be used in combination with other cyan couplers.

To the coupler of the present invention, there may be similarly applied methods and techniques used for common dye-forming couplers.

The coupler of the present invention may be used as a material for forming color photographs according to any developing method such as a coupler-in-developer type developing method and a coupler-in-emulsion type developing method. When the coupler of the present invention is used for a coupler-in-developer type developing method, it may be used by dissolving it in an alkaline aqueous solution or an organic solvent and adding the solution to a developing processing solution.

When the coupler of the present invention is used as a material for forming color photographs according to a coupler-in-emulsion type developing method, it may be used by incorporating it into a light-sensitive photographic material.

There may be typically preferably used a method in which the coupler of the present invention is formulated to a silver halide emulsion, and the emulsion is coated on a support to prepare a light-sensitive color material.

The coupler of the present invention is used in, for example, light-sensitive color photographic materials such as color negative and positive films and a color printing paper.

The light-sensitive material using the coupler of the present invention including the color printing paper may be for monochrome or for multicolor. In the light-sensitive material for multicolor, the coupler of the present invention may be contained in any layer, but it is generally contained in a red-sensitive silver halide emulsion layer. The light-sensitive material for multicolor has dye image-forming constitutional units having the respective sensitivities to the three primary color regions of a spectrum. Each constitutional unit may comprise a single layer or multilayer emulsion layer having sensitivity to a specific region of a spectrum.

The typical light-sensitive material for multicolor comprises a cyan dye image-forming constitutional unit comprising at least one red-sensitive silver halide emulsion layer containing at least one cyan coupler, a magenta dye image-forming constitutional unit comprising at least one green-sensitive silver halide emulsion layer containing at least one magenta coupler and a yellow dye image-forming constitutional unit comprising at least one blue-sensitive silver halide emulsion layer containing at least one yellow coupler which are provided on a support.

The light-sensitive material may have additional layers, for example, a filter layer, an intermediate layer, a protective layer and a subbing layer. The coupler of the present invention can be incorporated into an emulsion according to a conventionally known method. For example, one coupler of the present invention or a combination thereof is dissolved in either a high boiling point organic solvent having a boiling point of 175° C. or higher such as tricresyl phosphate and dibutyl phthalate or a low boiling point solvent such as butyl acetate and butyl propionate, or a mixture thereof, if necessary; the resulting solution is mixed with a gelatin aqueous solution containing a surfactant; the mixture is emulsified by a high speed rotary mixer or a colloid mill; and then the emulsion is added to silver halide to prepare a silver halide emulsion to be used in the present invention.

The silver halide composition to be preferably used in the light-sensitive material using the coupler of the present invention is silver chloride, silver chlorobromide or silver chloroiodobromide. Further, the composition may be a mixture obtained by combining them such as a mixture of silver chloride and silver bromide. This is because when the silver halide emulsion is used for a color printing paper, particularly rapid developability is demanded, so that the halogen composition of silver halide preferably contains chlorine atom, which is particularly preferably silver chloride, silver chlorobromide or silver chloroiodobromide containing at least 1% of silver chloride.

The silver halide emulsion can be chemically sensitized according to a conventional manner. Further, it can be optically sensitized to a desired wavelength region. To the silver halide emulsion, a compound known as an antifoggant or a stabilizer in the photographic field may be added for the purposes of preventing fog during preparing and storing the light-sensitive material or during photographic processing, and/or maintaining photographic properties stably.

In the light-sensitive color material using the coupler of the present invention, there may be used a color antifoggant, a dye image stabilizer, a UV absorber, an antistatic agent, a matting agent and a surfactant which are generally used in a light-sensitive material.

As to these additives, reference may be made to, for example, the description in Research Disclosure, Vol. 176, pp. 22 to 31 (December, 1978).

The light-sensitive color photographic material using the coupler of the present invention can form a dye by carrying out color development processing known in this field of the art.

The light-sensitive color photographic material using the coupler of the present invention may contain a color developing agent as such or as a precursor thereof in a hydrophilic colloid layer, and may be processed by an alkaline activating bath.

The light-sensitive color photographic material using the coupler of the present invention are subjected to bleaching processing and fixing processing after color development. Bleaching processing and fixing processing may be carried out at the same time.

After fixing processing, washing processing is generally carried out. Further, stabilizing processing may be carried out as a substitute for washing processing, or both processings may be used in combination.

EXAMPLES

In the following, the present invention is described in detail by referring to Examples, but the present invention is not limited thereto.

Example 1

On a paper support having the both surfaces laminated with polyethylene were provided by coating the following respective layers successively from the support side to prepare a red-sensitive light-sensitive color material Sample 1. The amounts of the compounds are values per 1 m² unless otherwise indicated (the amount of silver halide is a value calculated on silver).

First layer: Emulsion layer

A red-sensitive emulsion layer comprising 1.2 g of gelatin, 0.30 g of a red-sensitive silver chlorobromide emulsion (containing 96 mole % of silver chloride) and $9.1 \times 10^{-4}$ mole of Comparative cyan coupler (a) dissolved in 1.35 g of dioctyl phosphate.

Comparative coupler (a)

[Chemical structure: A phenol derivative with OH, Cl, H$_3$C, Cl substituents, and NHCOCHO(C$_2$H$_5$) linked to a benzene ring with two C$_5$H$_{11}$(t) groups]

Second layer: Protective layer

A protective layer containing 0.50 g of gelatin. As a hardener, 0.017 g of 2,4-dichloro-6-hydroxy-s-triazine sodium salt was added per 1 g of gelatin.

Next, the procedures were carried out in the same manner as in the case of Sample 1 except for changing Comparative coupler (a) to the couplers shown in Table 1 (amounts added were equimolar amounts of Comparative coupler (a)) to prepare Samples 2 to 8 of the present invention.

Samples 1 to 8 obtained as described above were subjected to wedge exposure according to a conventional manner, respectively, and then to development processing according to the following steps.

| (Development processing steps) | | |
|---|---|---|
| Color development | 38° C. | 3 min 30 sec |
| Bleach fixing | 38° C. | 1 min 30 sec |
| Stabilizing processing or washing processing | 25° C. to 30° C. | 3 min |
| Drying | 75° C. to 80° C. | 2 min |

The processing solutions used in the respective processing steps had the compositions shown below.

| (Color developing solution) | |
|---|---|
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-Methyl-4-amino-N-ethyl-N-(β-methane-sulfonamidoethyl)aniline sulfate | 5.5 g |
| Fluorescent brightener (4,4'-diaminostil-benedisulfonic acid derivative) | 1.0 g |
| Potassium hydroxide | 2.0 g |

Made up to 1 liter in total with addition of water, and adjusted to pH 10.20.

| (Bleach fixing solution) | |
|---|---|
| Ferric ammonium ethylenediaminetetra-acetate dihydrate | 60 g |
| Ethylenediaminetetraacetic acid | 3 g |
| Ammonium thiosulfate (70% solution) | 100 ml |
| Ammonium sulfite (40% solution) | 27.5 ml |

Adjusted to pH 7.1 with potassium carbonate or glacial acetic acid, and made up to 1 liter with addition of water.

| (Stabilizing solution) | |
|---|---|
| 5-Chloro-2-methyl-4-isothiazolin-3-one | 1.0 g |
| Ethylene glycol | 10 g |

Made up to 1 liter with addition of water.

For Samples 1 to 8 processed as described above, the density was measured by using a densitometer, Model KD-7 (trade name, manufactured by Konica Corporation). Further, the above respective processed samples were left to stand under high temperature and high humidity atmosphere (60° C., a relative humidity of 80%) for 14 days, and the heat and humidity resistance of the dye images was examined.

After the respective samples were irradiated by a xenon fade meter for 10 days, the density was measured to determine the light resistance. The results are shown in Table 1. In Table 1, the heat and humidity resistance and light resistance of the dye images are shown by dye remaining % after the heat and humidity resistance and light resistance tests with the initial density being 1.0.

TABLE 1

| | | Dye remaining rate (%) | |
|---|---|---|---|
| Sample No. | Coupler used | Heat and humidity resistance | Light resistance |
| 1 | Comparative (a) | 60 | 81 |
| 2 | Present invention 3 | 87 | 85 |
| 3 | Present invention 6 | 91 | 83 |
| 4 | Present invention 8 | 90 | 82 |
| 5 | Present invention 12 | 86 | 86 |
| 6 | Present invention 14 | 87 | 85 |
| 7 | Present invention 19 | 91 | 83 |
| 8 | Present invention 24 | 90 | 84 |

As clearly seen from the results shown in Table 1, all of the samples using the couplers of the present invention had high dye remaining rates as compared with the sample using the comparative coupler, and it can be seen that the present samples are excellent in heat and humidity resistance and light resistance and have high fastness.

EXAMPLE 2

On a subbed triacetate film were provided by coating the following respective layers successively from the support side to prepare a red-sensitive light-sensitive color material (Sample 9). The amounts of the compounds are values per 1 m² unless otherwise indicated (the amount of silver halide is a value calculated on silver).

First layer: Emulsion layer

A red-sensitive emulsion layer comprising 1.4 g of gelatin, 1.5 g of a red-sensitive silver iodobromide emulsion (containing 4 mole % of silver iodide) and $8.0 \times 10^{-4}$ mole of Comparative cyan coupler (b) dissolved in 1.1 g of tricresyl phosphate.

Comparative cyan coupler (b)

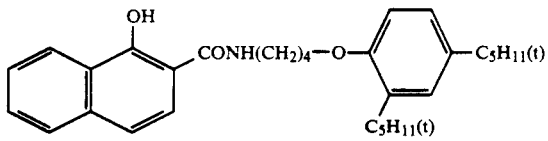

Second layer: Protective layer

A protective layer containing 1.5 g of gelatin. As a hardener, 0.017 g of 2,4-dichloro-6-hydroxy-s-triazine sodium salt was added per 1 g of gelatin.

Next, the procedures were carried out in the same manner as in the case of Sample 9 except for changing Comparative coupler (b) to the couplers shown in Table 2 (amounts added were equimolar amounts of the comparative coupler) to prepare Samples 10 to 16 of the present invention.

The film samples obtained were subjected to wedge exposure according to a conventional manner, and to color development according to the following color processing steps.

| Processing step | Processing temperature | Processing time |
|---|---|---|
| Color development | 38° C. | 3 min 15 sec |
| Bleaching | 38° C. | 6 min 30 sec |
| Washing | 38° C. | 3 min 15 sec |
| Fixing | 38° C. | 6 min 30 sec |
| Washing | 38° C. | 3 min 15 sec |
| Stabilizing | 38° C. | 1 min 30 sec |
| Drying | | |

The processing solutions used in the respective processing steps had the compositions shown below.

| (Color developing solution) | |
|---|---|
| 4-Amino-3-methyl-N-ethyl-N-(β-hydroxyethyl)aniline sulfate | 4.75 g |
| Anhydrous sodium sulfite | 4.25 g |
| Hydroxylamine 1/2 sulfate | 2.0 g |
| Anhydrous calcium carbonate | 37.5 g |
| Sodium bromide | 1.3 g |
| Nitrilotriacetic acid.trisodium salt (monohydrate) | 2.5 g |
| Potassium hydroxide | 1.0 g |

Made up to 1 liter with addition of water, and adjusted to pH 10.6 by using sodium hydroxide.

| (Bleaching solution) | |
|---|---|
| Ferric ammonium ethylenediaminetetraacetate | 100.0 g |
| Diammonium ethylenediaminetetraacetate | 10.0 g |
| Ammonium bromide | 150.0 g |
| Glacial acetic acid | 10.0 g |

Made up to 1 liter with addition of water, and adjusted to pH 6.0 with aqueous ammonia.

| (Fixing solution) | |
|---|---|
| Ammonium thiosulfate | 175.0 g |
| Anhydrous sodium sulfite | 8.6 g |
| Sodium metasulfite | 2.3 g |

Made up to 1 liter with addition of water, and adjusted to pH 6.0 with acetic acid.

| (Stabilizing solution) | |
|---|---|
| Formalin (37% aqueous solution) | 1.5 ml |
| Konidax (trade name, produced by Konica Corporation) | 7.5 ml |

Made up to 1 liter with addition of water.

For Samples 9 to 16 processed as described above, the transmission density was measured by using a densitometer, Model KD-7R (trade name, manufactured by Konica Corporation). Further, the above respective processed samples were left to stand under high temperature and high humidity atmosphere (60° C., a relative humidity of 80%) for 14 days, and the heat and humidity resistance of the dye images was examined.

After the respective samples were irradiated by a xenon fade meter for 10 days, the light resistance was examined. The results are shown in Table 2. In Table 2, the heat and humidity resistance and light resistance of the dye images are shown by dye remaining % after the heat and humidity resistance and light resistance tests with the initial density being 1.0.

TABLE 2

| | | Dye remaining rate (%) | |
|---|---|---|---|
| Sample No. | Coupler used | Heat and humidity resistance | Light resistance |
| 9 | Comparative (b) | 70 | 80 |
| 10 | Present invention 4 | 88 | 80 |
| 11 | Present invention 5 | 91 | 82 |
| 12 | Present invention 10 | 89 | 83 |
| 13 | Present invention 15 | 87 | 85 |
| 14 | Present invention 17 | 92 | 86 |
| 15 | Present invention 21 | 90 | 83 |
| 16 | Present invention 22 | 87 | 85 |

As clearly seen from the results shown in Table 2, all of the samples using the couplers of the present invention had high dye remaining rates as compared with the sample using the comparative coupler, and it can be seen that the present samples are excellent in heat and humidity resistance and light resistance and have high fastness.

EXAMPLE 3

On a triacetyl cellulose film support were provided by coating the following respective layers successively from the support side to prepare red-sensitive color reversal light-sensitive photographic materials 17 to 22.

First layer: Emulsion layer

A red-sensitive emulsion layer comprising 1.4 g of gelatin, 0.5 g of a red-sensitive silver chlorobromide emulsion (containing 96 mole % of silver chloride) and $9.1 \times 10^{-4}$ mole of the coupler shown in Table 3 dissolved in 1.5 g of dibutyl phthalate.

Second layer: Protective layer

A protective layer containing 0.5 g of gelatin. As a hardener, 0.017 g of 2,4-dichloro-6-hydroxy-s-triazine sodium salt was added per 1 g of gelatin.

The samples obtained as described above were subjected to wedge exposure according to a conventional manner, respectively, and then to development processing according to the following steps.

| (Reversal processing step) | | |
| --- | --- | --- |
| Step | Time | Temperature |
| First development | 6 min | 38° C. |
| Washing | 2 min | 38° C. |
| Reversing | 2 min | 38° C. |
| Color development | 6 min | 38° C. |
| Adjustment | 2 min | 38° C. |
| Bleaching | 6 min | 38° C. |
| Fixing | 4 min | 38° C. |
| Washing | 4 min | 38° C. |
| Stabilizing | 1 min | 38° C. |
| Drying | | Normal temperature |

The processing solutions had the compositions shown below.

| (First developing solution) | |
| --- | --- |
| Sodium tetrapolyphosphate | 2 g |
| Sodium sulfite | 20 g |
| Hydroquinone.monosulfonate | 30 g |
| Sodium carbonate (monohydrate) | 30 g |
| 1-Phenyl-4-methyl-4-hydroxymethyl-3-pyrazolidone | 2 g |
| Potassium bromide | 2.5 g |
| Potassium thiocyanate | 1.2 g |
| Potassium iodide (0.1% solution) | 2 ml |

Made up to 1 liter with addition of water.

| (Reversing solution) | |
| --- | --- |
| Nitrilotrimethylenesulfonic acid.hexasodium salt | 3 g |
| Stannous chloride (dihydrate) | 1 g |
| p-Aminophenol | 0.1 g |
| Sodium hydroxide | 5 g |
| Glacial acetic acid | 15 ml |

Made up to 1 liter with addition of water.

| (Color developing solution) | |
| --- | --- |
| Sodium tetrapolyphosphate | 2 g |
| Sodium sulfite | 7 g |
| Sodium tertiary phosphate (dodecahydrate) | 36 g |
| Potassium bromide | 1 g |
| Potassium iodide (0.1% solution) | 90 ml |
| Sodium hydroxide | 3 g |
| Citrazinic acid | 1.5 g |
| N-Ethyl-N-($\beta$-methanesulfonamidoethyl)-3-methyl-4-aminoaniline.sulfate | 11 g |
| Ethylenediamine | 3 g |

Made up to 1 liter with addition of water.

| (Adjusting solution) | |
| --- | --- |
| Sodium sulfite | 12 g |
| Sodium ethylenediaminetetraacetate (dihydrate) | 8 g |
| Thioglycerin | 0.4 ml |
| Glacial acetic acid | 3 ml |

Made up to 1 liter with addition of water.

| (Bleaching solution) | |
| --- | --- |
| Sodium ethylenediaminetetraacetate (dihydrate) | 2.0 g |
| Iron (III) ammonium ethylenediaminetetraacetate (dihydrate) | 120.0 g |
| Potassium bromide | 100.0 g |

Made up to 1 liter with addition of water.

| (Fixing solution) | |
| --- | --- |
| Ammonium thiosulfate | 80.0 g |
| Sodium sulfite | 5.0 g |
| Sodium bisulfite | 5.0 g |

Made up to 1 liter with addition of water.

| (Stabilizing solution) | |
| --- | --- |
| Formalin (37% by weight) | 5.0 ml |
| Konidax (trade name, produced by Konica Corporation) | 5.0 ml |

Made up to 1 liter with addition of water.

The above respective samples processed as described above, the heat and humidity resistance and light resistance of the dye images were examined in the same manner as in Example 2. The results are shown in Table 3.

TABLE 3

| | | Dye remaining rate (%) | |
| --- | --- | --- | --- |
| Sample No. | Coupler used | Heat and humidity resistance | Light resistance |
| 17 | Comparative (a) | 59 | 81 |
| 18 | Present invention 7 | 91 | 83 |
| 19 | Present invention 9 | 87 | 82 |
| 20 | Present invention 13 | 88 | 81 |
| 21 | Present invention 20 | 89 | 84 |
| 22 | Present invention 25 | 90 | 84 |

As clearly seen from Table 3, all of the samples using the couplers of the present invention had high dye remaining rates as compared with the sample using the comparative coupler, and it can be seen that the present samples are excellent in heat and humidity resistance and light resistance and have high fastness.

EXAMPLE 4

On a transparent polyethylene terephthalate film support was provided by coating a heat-processable light-sensitive layer comprising the following constitutional components per 1 m² of the support to prepare a heat-processable light-sensitive material.

| Benztriazole silver | 0.6 g |
| --- | --- |
| Gelatin | 3.0 g |
| Reducing agent*[1] | 0.97 g |
| Coupler 11 | 1.0 g |
| Silver iodobromide (calculated on silver) | 0.45 g |
| Polyvinyl pyrrolidone | 1.0 g |

| -continued | |
|---|---|
| Benztriazole | 0.02 g |
| Inhibitor*2 | 0.06 g |
| Heat solvent*3 | 4.5 g |

After the above light-sensitive material was subjected to imagewise exposure, the material was superposed on an image receiving material obtained by providing polyvinyl chloride on a photographic baryta paper by coating, and then subjected to thermal development at 150° C. for 1 minute to obtain a good cyan color transferred image on the image receiving material.

Reducing agent*1

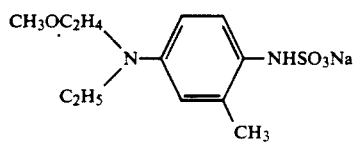

Inhibitor*2

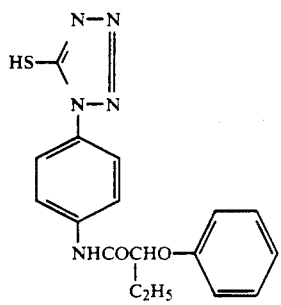

Heat solvent*3

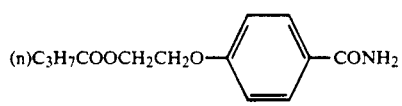

It can be seen that the dye image formed by using the coupler of the present invention has good fastness to heat, humidity and light. Further, it can be seen that the coupler of the present invention is also useful as a dye-providing substance of a heat-processable light-sensitive material.

We claim:

1. A silver halide photographic material comprising a support, and provided thereon, at least one silver halide emulsion layer containing
a photographic coupler represented by Formula 1:

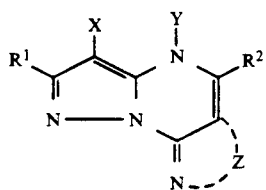

wherein $R^1$ and Y represent hydrogen or a substituent; $R^2$ is alkyl, aryl, alkenyl, cycloalkenyl, alkynyl, or a heterocyclic ring group, Z represents a nonmetallic atomic group necessary for forming a 5- to 7-membered heterocyclic ring, and said 5- to 7-membered ring may have a substituent(s); and x represents hydrogen atom or a substituent which is eliminatable by the reaction with an oxidized product of a color developing agent.

2. The photographic material of claim 1 wherein said coupler is at least one selected from the group consisting of:

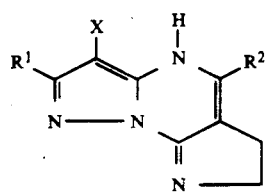

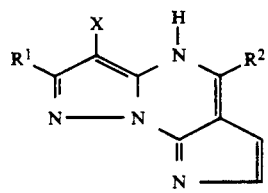

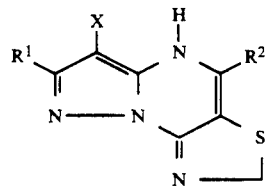

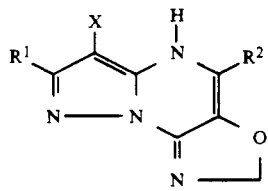

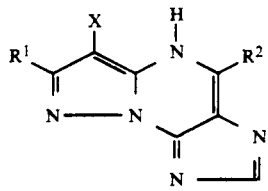

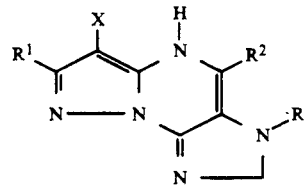

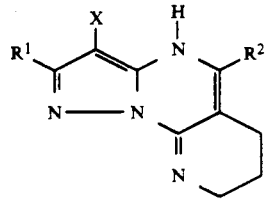

-continued

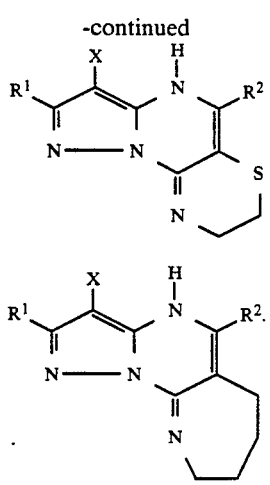

3. The photographic material of claim 1 wherein $R^1$ is an alkyl, aryl, anilino, acylamino, sulfonylamido, alkylthio, arylthio, alkenyl or cycloalkyl group.

4. The photographic material of claim 1 wherein X is a hydrogen atom or chlorine atom.

5. The photographic material of claim 1 wherein Y is a hydrogen atom.

6. The photographic material of claim 1 wherein said coupler is contained in an amount of $1 \times 10^{-3}$ mole to 1 mole per mole of silver halide.

7. The photographic material of claim 1 wherein said coupler is at least one selected from the group consisting of:

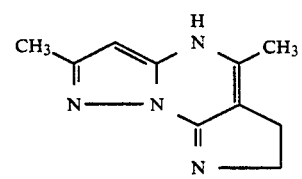
(1)

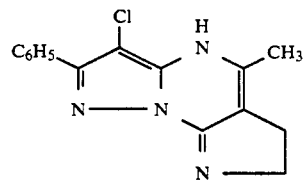
(2)

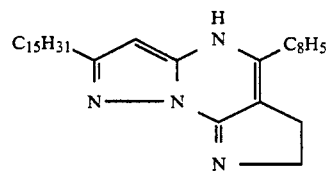
(3)

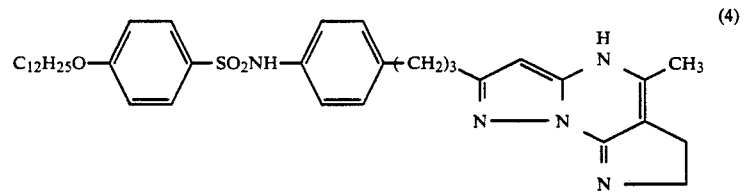
(4)

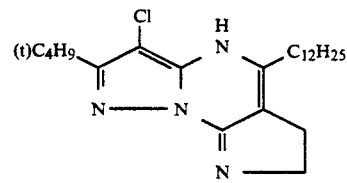
(5)

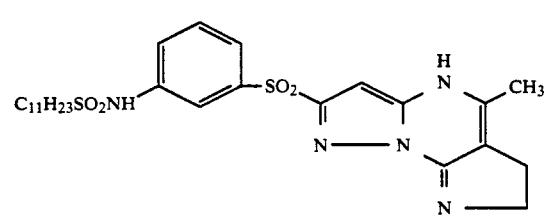
(6)

-continued
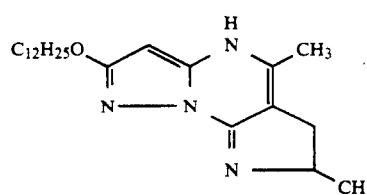 (7)
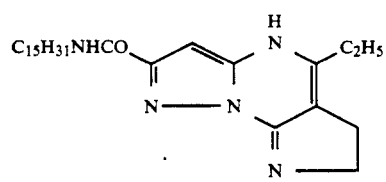 (8)
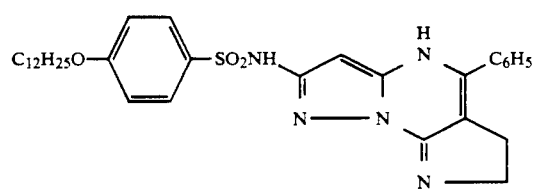 (9)
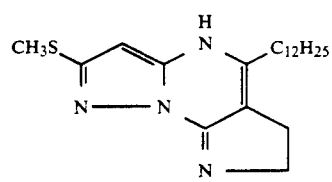 (10)
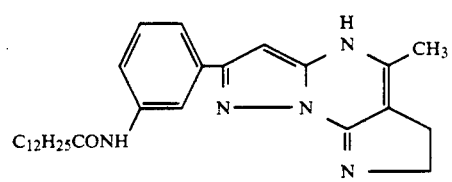 (11)
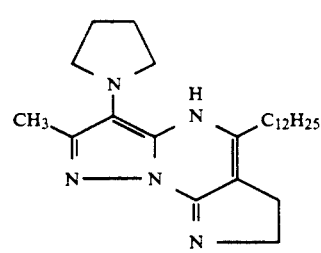 (12)
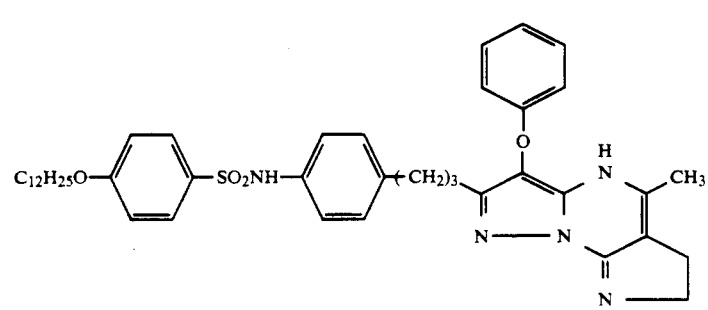 (13)

-continued
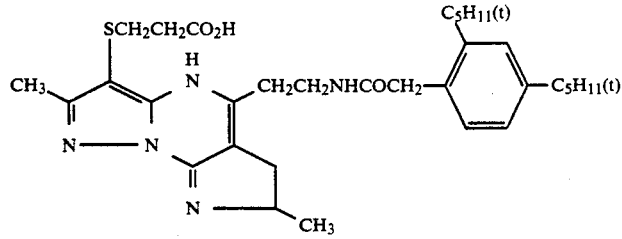 (14)
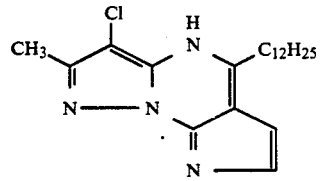 (15)
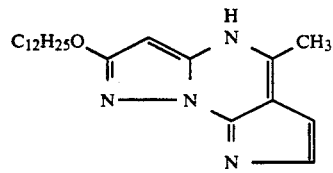 (16)
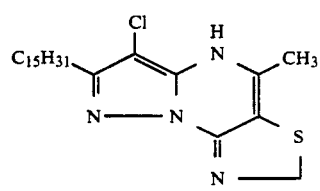 (17)
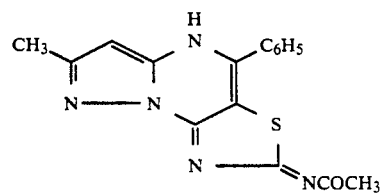 (18)
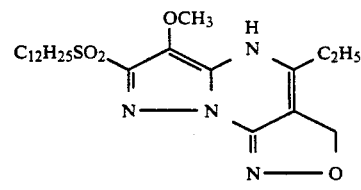 (19)
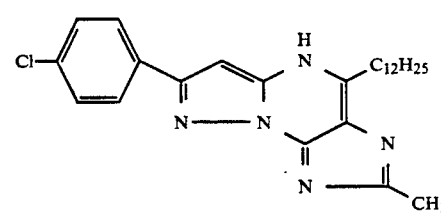 (20)
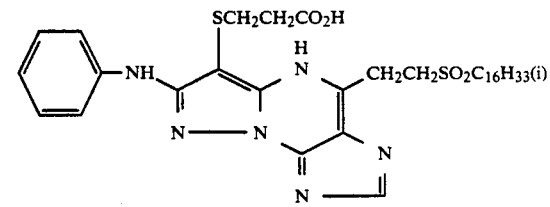 (21)

-continued

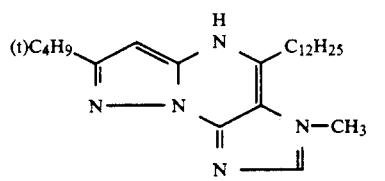
(22)

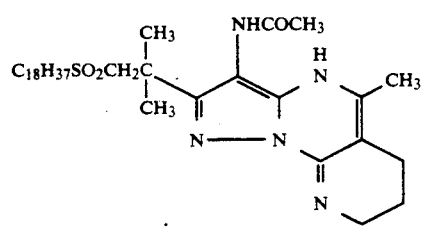
(23)

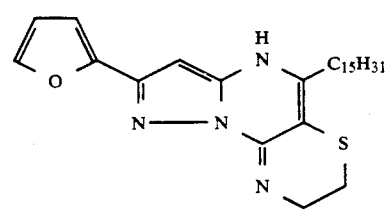
(24)

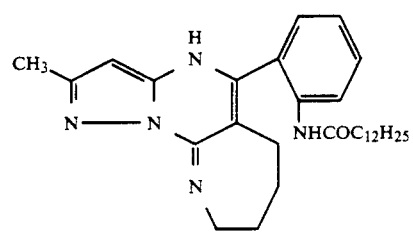
(25)

8. A light-sensitive silver halide color photographic material comprising
a photographic coupler represented by the formula 1:

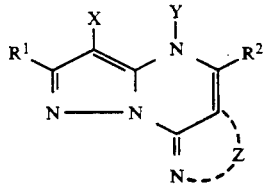

wherein $R^1$ and Y represent a hydrogen atom or a substituent; $R^2$ is an alkyl, aryl, alkenyl, cycloalkenyl, alkynyl or heterocyclic ring group, Z represents a non-metallic atomic group necessary for forming a 5- to 7-membered heterocyclic ring, and said 5- to 7-membered ring may have a substitutent(s); and X represents hydrogen atom or a substituent which is eliminatable by the reaction with an oxidized product of a color developing agent.

9. A heat-processable light-sensitive material comprising
a photographic coupler represented by the formula 1:

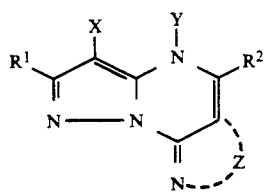

wherein $R^1$ and Y represent a hydrogen atom or a substituent; $R^2$ is an alkyl, aryl, alkenyl, cycloalkenyl, alkynyl or heterocyclic ring group, Z represents a non-metallic atomic group necessary for forming a 5- to 7-membered heterocyclic ring, and said 5- to 7-membered ring may have a substituent(s); and X represents hydrogen atom or a substituent which is eliminatable by the reaction with an oxidized product of a color developing agent.

* * * * *